United States Patent
Blondel et al.

(10) Patent No.: US 12,426,984 B2
(45) Date of Patent: Sep. 30, 2025

(54) AUGMENTED-REALITY NAVIGATION SYSTEM FOR A MEDICAL ROBOT

(71) Applicant: Quantum Surgical, Montpellier (FR)

(72) Inventors: Lucien Blondel, Montpellier (FR); Bertin Nahum, Castelnau-le-Lez (FR); Fernand Badano, Lyons (FR)

(73) Assignee: Quantum Surgical, Montpellier (FR)

( * ) Notice: Subject to any disclaimer, the term of this patent is extended or adjusted under 35 U.S.C. 154(b) by 248 days.

(21) Appl. No.: 18/248,251

(22) PCT Filed: Oct. 5, 2021

(86) PCT No.: PCT/FR2021/051719
§ 371 (c)(1),
(2) Date: Apr. 7, 2023

(87) PCT Pub. No.: WO2022/074325
PCT Pub. Date: Apr. 14, 2022

(65) Prior Publication Data
US 2023/0372050 A1 Nov. 23, 2023

(30) Foreign Application Priority Data
Oct. 8, 2020 (FR) .................................. FR2010309

(51) Int. Cl.
*A61B 34/20* (2016.01)
*A61B 34/30* (2016.01)
(Continued)

(52) U.S. Cl.
CPC .............. *A61B 90/36* (2016.02); *A61B 34/20* (2016.02); *A61B 34/30* (2016.02); *A61B 90/50* (2016.02);
(Continued)

(58) Field of Classification Search
None
See application file for complete search history.

(56) References Cited

U.S. PATENT DOCUMENTS

2009/0156951 A1 6/2009 Averbuch
2020/0405403 A1* 12/2020 Shelton, IV ....... A61B 17/3421

FOREIGN PATENT DOCUMENTS

| WO | 2018032083 A1 | 2/2018 |
|---|---|---|
| WO | 2019051464 A1 | 3/2019 |
| WO | 2020096810 A1 | 5/2020 |

OTHER PUBLICATIONS

Qian et al., "ARssist: Augmented Reality on a Head-Mounted Display for the first assistant in robotic surgery", 2018. (Year: 2018).*

(Continued)

*Primary Examiner* — Nicholas R Wilson
(74) *Attorney, Agent, or Firm* — ArentFox Schiff LLP (57) ABSTRACT

An augmented-reality navigation system is used to assist a practitioner during a surgical operation on an anatomical structure of interest of a patient. The operation is planned on a pre-operational medical image. The navigation system comprises a camera that is intended to be worn by the practitioner on his head, a display device for displaying, in real-time, the real images acquired by the camera and an augmented-reality content superposed on the real images, and a control unit connected to the camera and to the display device. The control unit is configured to generate a predictive model of the movement of a marker placed in proximity to the anatomical structure of interest on the basis of the movement followed by the marker during one or more respiratory cycles of the patient. The predictive model is used to determine an opportune moment to perform the surgical operation as planned on the pre-operational image, (Continued)

and/or to display in augmented reality a three-dimensional anatomical model of the anatomical structure of interest.

20 Claims, 6 Drawing Sheets

(51) Int. Cl.
*A61B 90/00* (2016.01)
*A61B 90/50* (2016.01)
*A61B 34/10* (2016.01)

(52) U.S. Cl.
CPC ... *A61B 2034/105* (2016.02); *A61B 2034/107* (2016.02); *A61B 2034/2055* (2016.02); *A61B 2090/365* (2016.02); *A61B 2090/3983* (2016.02); *A61B 2090/502* (2016.02)

(56) References Cited

OTHER PUBLICATIONS

Wu et al., "Real-Time Advanced Spinal Surgery Via Visible Patient Model and Augmented Reality System" 2013. (Year: 2013).*
Nicolau et al., "Augmented Reality in Laproscopic Surgical Oncology" Elsevier, 2011. (Year: 2011).*
Baxter et al., "Training for Planning Tumor Resection: Augmented Reality and Human Factors", IEEE, 2015. (Year: 2015).*
International Search Report mailed, Jan. 24, 2022, for PCT/FR2021/051719.

* cited by examiner

AUGMENTED-REALITY NAVIGATION SYSTEM FOR A MEDICAL ROBOT

CROSS-REFERENCE TO RELATED APPLICATIONS

This application is a National Phase of PCT/FR2021/051719, filed on Oct. 5, 2021, which claims priority to FR Patent Application No FR2010309, filed on Oct. 8, 2020, the disclosures of which are hereby incorporated by reference in their entireties.

FIELD OF THE INVENTION

The present invention relates to the field of the equipment used in the context of robot-assisted minimally-invasive surgical interventions. In particular, the invention relates to an augmented-reality navigation system intended to collaborate with a medical robot to assist a practitioner in performing a surgical intervention.

PRIOR ART

Minimally-invasive surgical interventions consist in inserting one or more medical instruments into an anatomy of interest of a patient. For example, a minimally invasive surgical intervention may aim to take a biopsy or to ablate a lesion such as a tumour.

In a minimally-invasive surgical intervention, the anatomy of interest of the patient is not generally visible to the practitioner with the naked eye. The insertion of a medical instrument is generally guided by medical imaging. In order to improve the precision with which the medical instrument can be inserted, minimally-invasive interventions may be assisted by a robot device. In order to make the anatomy of interest visible to the practitioner, it is possible to convert the content of a medical image of the anatomy of interest into augmented-reality content overlaid on the body of the patient. In order to monitor the insertion of the medical instrument into the anatomy of interest during the surgical intervention it is, however, necessary to obtain numerous medical images, and this entails using invasive means (for example an endoscope) or else medical imaging devices that expose the patient to radiation throughout the duration of the surgical intervention.

In the particular case of soft organs, the medical images are unable to reproduce the movements associated with respiration, with local deformations of the organ as a result of the insertion of the medical instrument, or else with the involuntary movements of the patient at the moment of intervention. Thus, the position of a lesion in an anatomy of interest may differ between the time of the acquisition of a medical image and the time of the intervention. If the insertion of the medical instrument is planned on the basis of the medical image, there is a risk that the lesion might not be reached precisely by the medical instrument.

The current means for assisting a practitioner in performing a minimally-invasive surgical intervention are therefore unable to allow the practitioner to take account, in a simple and reliable way, of the movements associated with the respiration of the patient, with internal deformations of the anatomy of interest, or with involuntary movements of the patient during the course of the surgical intervention.

SUMMARY OF THE INVENTION

An objective of the present invention is to overcome all or some of the disadvantages of the prior art, notably those set out hereinabove.

To that end, and according to a first aspect, the present invention proposes an augmented-reality navigation system for assisting a practitioner when performing a surgical intervention on an anatomy of interest of a patient. Said system notably comprises:
  a camera for acquiring real images, said camera being intended to be worn by the practitioner on their head,
  a display device for displaying, in real-time, the real images acquired by the camera together with augmented-reality content overlaid on said real images,
  a control unit connected to the camera and to the display device.

Said control unit of the augmented-reality navigation system is configured to:
  detect, on the real images, the position of a marker placed on the patient in the proximity of said anatomy of interest,
  record the movement followed by the marker during a recording period corresponding to one or more respiratory cycles of the patient,
  determine the position of the marker at a first instant belonging to said recording period and corresponding to an instant of acquisition of a pre-intervention medical image of the anatomy of interest of the patient by a medical imaging device,
  formulate a predictive model of the movement of the marker from the movement followed by the marker during the recording period.

In the present application, and unless indicated otherwise, the term "position" encompasses the notion of both location and orientation of an object in a given frame of reference which is generally a three-dimensional coordinate system. The term "pose" is used in English-language literature to indicate this combination of the position and orientation of an object in space. In the present application, and unless indicated otherwise, the term "position" is therefore equivalent to the term "position/orientation".

The minimally-invasive surgical intervention consists, for example, in inserting, into an anatomy of interest of a patient (for example a soft organ such as the liver, a lung, a kidney or a rigid structure such as a bone), one or more medical instruments for taking a biopsy, for ablating a lesion (for example a tumour), for positioning an implant (for example a screw, a plate, a prosthesis), or for inserting other materials (for example cement or an artificial disk). In this type of intervention, the anatomy of interest is not visible to the naked eye.

Advantageously, the camera of the augmented-reality navigation system is worn by the practitioner on their head so that the camera maintains a direct line of sight of the patient (and notably so that the practitioner cannot obstruct this direct line of sight).

The augmented-reality navigation system allows information to be displayed on the display device in the form of augmented-reality content, which means to say that this information is overlaid on the real images, and would not otherwise be visible to the practitioner. Advantageously, the display device may also be worn by the practitioner on their head, directly in front of the eyes of the practitioner (for example in the form of a mask/facepiece, of a headset or of spectacles/goggles). Such devices allow the practitioner to read the information from the display device without averting their gaze from the patient. This also makes it possible to limit the size of the room in which intervention is performed. However, there is nothing to prevent the display device from being, in variants, a screen visible to several individuals present in the room in which the intervention is being performed (for example a screen fixed to the operating table above the patient).

The control unit may also be worn by the practitioner on their head. Alternatively, the control unit may belong to an entity distinct from the entity worn by the practitioner on their head. The control unit is connected to the camera and to the display device, for example via wired communications means or via wireless communications means.

The marker placed on the patient in proximity to the anatomy of interest may be identified by the augmented-reality navigation system thanks to one or more optical markers of known geometry. This marker also comprises radiopaque markers of known geometry which are visible on a medical image acquired by a medical imaging device (for example by computed tomography, by magnetic resonance, by ultrasound, by tomography, by position emission tomography, etc.). The pre-intervention medical image is, for example, acquired at an instant at which the respiration of the patient is blocked. However, there is nothing to prevent, in another example, the pre-intervention medical image from being acquired at an instant at which the patient is breathing freely, for example when the respiration reaches a plateau at the end of inspiration or at the end of expiration (when one of these plateaux is reached, the movement associated with the respiration of the patient is negligible for two to three seconds).

It is possible to plan the surgical intervention on the basis of the pre-intervention medical image, and notably to define the position that the medical instrument needs to adopt with respect to the position of the marker in order to perform said surgical intervention. However, the position of the anatomy of interest may vary with respect to the position of the marker because of the movements associated with the respiration of the patient, with internal deformations of the organ or with involuntary movements of the patient at the moment of intervention. It is therefore appropriate to ensure that, when the surgical intervention is performed, the patient is in the same position or in the same phase of the respiratory cycle as they were at the time at which the pre-intervention medical image was acquired.

In the invention, the control unit is configured to record the movement followed by the marker during one or more respiratory cycles of the patient, to determine the position of the marker at the instant at which the pre-intervention medical image is acquired, and to formulate a predictive model of the movement of the marker from the recorded movement.

Such measures notably make it possible to plan the surgical intervention on the pre-intervention medical image and to ensure that, at the moment of insertion of the medical instrument, the marker is in the same position as the position of the marker at the moment at which the pre-intervention medical image was acquired (or in other words, to ensure that, at the moment of insertion of the medical instrument, the patient is in the same position or in the same phase of the respiratory cycle as they were at the moment at which the pre-intervention medical image was acquired).

Furthermore, the predictive model of the movement of the marker can be used to continuously, and in real-time, update a three-dimensional anatomical model of the anatomy of interest, which model is generated from the pre-intervention medical image. This anatomical model can then be displayed on the display device in the form of augmented-reality content overlaid on the real images.

In its simplest form, the predictive model corresponds to the movement of the marker recorded during a respiratory cycle, or during several respiratory cycles. Advantageously, the predictive model may, however, be formulated using statistical calculations regarding the positions adopted by the marker during several consecutive respiratory cycles. It is notably conceivable to resort to machine-learning algorithms in order to formulate the predictive model.

The medical imaging device is an entity distinct from the augmented-reality navigation system. There are various conceivable synchronization means so that the augmented-reality navigation system detects the instant at which the pre-intervention medical image is acquired.

The augmented-reality navigation system detects the position of the marker on the real images. This detection of the position of the marker may potentially be facilitated or made more reliable by an optical navigation device (stereoscopic camera, time-of-flight camera, etc.) or an electromagnetic navigation device.

In particular embodiments, the invention may further comprise one or more of the following features, considered in isolation or in any technically possible combinations.

In particular embodiments, the control unit is further configured to:
  determine, from the predictive model, a second instant corresponding to a candidate instant of insertion of a medical instrument into the anatomy of interest of the patient,
  compare the position of the marker at the first instant with the position of the marker at the second instant,
  display a result of the comparison on the display device in the form of augmented-reality content overlaid on the real images.

Comparing the position of the marker at the first instant (which corresponds to the instant of acquisition of the pre-intervention medical image during the recording period) with the position of the marker at the second instant (which corresponds to the insertion of the medical instrument into the anatomy of interest) then makes it possible to check whether the marker is in the same position as the position occupied by the marker at the moment at which the pre-intervention medical image was acquired (or in other words to check whether, at the moment of insertion of the medical instrument, the patient is in the same phase of the respiratory cycle as they were at the moment at which the pre-intervention medical image was acquired). The second instant corresponds for example to an instant at which the respiration of the patient is blocked. However, there is nothing to prevent the patient from breathing freely during the intervention. The second instant may be determined using the predictive model by synchronizing the movement of the marker as caused by the respiration of the patient, with the predictive model.

In particular embodiments, the control unit is further configured to receive the pre-intervention medical image from the medical imaging device and to generate, from the pre-intervention medical image, a three-dimensional anatomical model of the anatomy of interest of the patient and to display said anatomical model on the display device in the form of augmented-reality content overlaid on the real images. The position of the anatomical model overlaid on the real images is updated continuously and in real time according to the predictive model of the movement of the marker and according to a biomechanical model of anatomical structures of the human body.

What is meant by a "biomechanical model" is a mathematical model of the various anatomical structures (muscles, tendons, bone structures, organs, vascular network, etc.) of the human body and therefore of the patient in the anatomical zone considered which makes it possible to model the deformations of said anatomical structures, together with the mechanical interactions between said anatomical structures. Such a biomechanical model therefore in particular makes it possible to determine the deformations and mechanical interactions (and therefore the movements) of the internal anatomical structures of the patient which are brought about, for example, by a modification to the outer envelope of said patient, a modification of the positions of the blood vessels of an organ, a modification to the outer envelope of an organ, etc. Such modifications may for example be brought about by the respiration of the patient (movement of the organs brought about by the movement of the rib cage and of the diaphragm), by a change in position of the patient (movement of the organs brought about by gravity), by contact with a medical instrument (local deformation), etc.

The movement of the marker is, for example, indicative of the movement of the rib cage of the patient as brought about by the respiration of the patient. The biomechanical model therefore makes it possible to define how the position of the anatomical model is impacted by these movements during the course of the respiratory cycles of the patient.

Using such measures, the practitioner is able to view the anatomy of interest on the display device "through" the outer envelope of the body of the patient even though the anatomy of interest is not visible to the naked eye because it is internal to the body of the patient.

In particular embodiments, the control unit is further configured to display, on the anatomical model, in the form of augmented-reality content overlaid on the real images, an intended path to be followed by a medical instrument, said path being updated in real time according to the position of the anatomical model.

The path that is to be followed by the medical instrument is data from the planning of the surgical intervention and determined for example from the pre-intervention medical image. This path notably defines the position that the medical instrument is to adopt with respect to the position of the marker in order to perform said surgical intervention. This path comprises, for example, a target point to be reached in a region to be treated (for example a tumour) within the anatomy of interest, and a point of entry of the medical instrument at the surface of the anatomy of interest.

In particular embodiments, the intended path to be followed by the medical instrument is defined beforehand on a preoperative medical image, and the control unit is configured to receive said preoperative medical image and to realign the preoperative image to the pre-intervention medical image in order to display the path on the anatomical model.

What is meant by a "preoperative" image is an image on which a pathology is diagnosed several days, several weeks or even several months prior to a surgical intervention for treating said pathology. What is meant by a "pre-intervention" image is an image acquired at the moment of the surgical intervention when the patient is installed on the intervention table but before the surgical action is performed (which is to say before the medical instrument is inserted).

In particular embodiments, the system further comprises an interaction device allowing the practitioner to target a particular location on the anatomical model and wherein the intended path to be followed by the medical instrument is defined by the practitioner using the interaction device.

In particular embodiments, the control unit is configured to segment at least one element on the anatomical model from among the following elements:

different anatomical structures within the anatomy of interest, a region to be treated within the anatomy of interest, an ablation region estimated from parameters of the surgical intervention, ablation margins for a region to be treated within the anatomy of interest and determined by comparing the region to be treated and the estimated ablation region, and to display said segmented element on the anatomical model in the form of augmented-reality content overlaid on the real images. The segmented element is then updated in real time according to the position of the anatomical model.

What is meant by "anatomical structures" is, for example, organs, bones, blood vessels, etc. A region to be treated corresponds, for example, to a tumour to be ablated. An ablation region may be estimated according to surgical intervention parameters such as, for example, a type of treatment, a type of medical instrument used for the treatment, a duration of the treatment, a power of the treatment, etc.

In particular embodiments, the control unit is configured to display, on the display device, in the form of augmented-reality content, at least one virtual configuration object regarding a surgical treatment parameter. The system comprises an interaction device allowing the practitioner to interact with said virtual configuration object in order to select a particular value for said parameter.

A virtual configuration object corresponds, for example, to a menu, to a button, to a multiple-choice listing, etc. making it possible to define one particular parameter value for the treatment that is to be performed.

In particular embodiments, the display device is intended to be worn by the practitioner at eye level.

In particular embodiments, the control unit is configured to modify the position of augmented-reality content according to the position of the head of the practitioner.

In particular embodiments, the position of the head of the practitioner is determined using a practitioner-head motion sensor or directly from the position of the marker on the real images.

A second aspect of the present invention relates to an assembly formed by an augmented-reality navigation system according to any one of the preceding embodiments and a medical robot for assisting a practitioner in a surgical intervention on an anatomy of interest of a patient. The medical robot comprises a mobile base, an articulated arm, and a control unit. One end of the articulated arm is fixed to the mobile base and the other end has a tool guide intended to hold a medical instrument. The control unit of the medical robot is configured to determine a configuration of the articulated arm that allows a surgical action to be performed with the medical instrument along a predetermined path. The configuration of the articulated arm is determined according to information relating to the position of the marker which information is transmitted by the navigation system.

The augmented-reality navigation system and the medical robot collaborate with one another. The augmented-reality navigation system and the medical robot for example comprise communication means for exchanging messages. These communication means may be of the wired or wireless type.

The augmented-reality navigation system transmits to the medical robot information relating to the position of the marker so that the medical robot can position its articulated arm in a configuration that allows the medical instrument to perform a surgical action along a predetermined path. The path that is to be followed by the medical instrument is data from the planning of the surgical intervention determined for example on the basis of the pre-intervention medical image.

The medical action may be performed by the practitioner (and in this case the articulated arm of the medical robot is used chiefly for guiding the medical instrument in order to assist the practitioner in performing the medical action) or directly by the medical robot.

In particular embodiments, the invention may further comprise one or more of the following features, considered in isolation or in any technically possible combinations.

In particular embodiments, the information relating to the position of the marker is an indication that the result of the comparison between the position of the marker at the first instant (which corresponds to the instant of acquisition of the pre-intervention medical image during the recording period) with the position of the marker at the second instant (which corresponds to a candidate instant for the insertion of the medical instrument into the anatomy of interest) meets a particular criterion.

For example, the respiration of the patient may be blocked for inserting the medical instrument. At the moment at which the respiration is blocked, if the position of the marker is sufficiently close to the position of the marker at the instant at which the pre-intervention medical image was acquired, then the augmented-reality navigation system transmits to the medical robot an indication that the intervention can take place as planned on the basis of the pre-intervention medical image (because the patient is in the same phase of the respiratory cycle as they were at the moment at which the pre-intervention medical image was acquired).

The indication may be transmitted by the augmented-reality navigation system after the practitioner has validated the result of the comparison or else automatically, for example if the difference in position is below a predetermined threshold.

In particular embodiments, the information relating to the position of the marker corresponds to a predictive model indicative of the position of the anatomical model during the respiratory cycles of the patient. The control unit of the medical robot is configured to adjust, continuously and in real time, the configuration of the articulated arm according to said predictive model indicative of the position of the anatomical model.

With such measures, the articulated arm is positioned in a configuration that allows the surgical intervention to be performed whatever the instant concerned in a respiratory cycle of the patient.

In particular embodiments, the control unit of the augmented-reality navigation system is configured to model an outer envelope of the body of the patient, to determine the position of the articulated arm or of the tool guide of the medical robot and to detect a situation in which there is a risk of collision when the distance between the tool guide and the outer envelope of the patient is below a predetermined threshold.

The outer envelope of the body of the patient is, for example, modelled on the basis of a detection of the contours of the body of the patient in the real images. Such measures may make it possible to continuously and in real time measure the distance between the articulated arm and the patient or the distance between the tool guide and the patient. Immediate measures may then be taken in order to avoid undesirable contact between the articulated arm or the tool guide and the patient when positioning the articulated arm (for example when the body-mass of the patient is greater than had been estimated when planning the intervention).

In particular embodiments, the control unit interrupts the movement of the articulated arm as soon as the distance between the articulated arm or the tool guide and the outer envelope of the patient is insufficient, for example less than 5 cm or even less than 1 cm.

In particular embodiments, the control unit of the augmented-reality navigation system is configured to detect a situation in which there is a risk of injury from the medical instrument when a deviation in the position of the marker with respect to the predictive model of the movement of the marker is above a predetermined threshold. Such measures make it possible to detect a situation in which the patient is making an unexpected movement during the course of the insertion of the medical instrument or when the medical instrument has been inserted but not yet released from the tool guide. Such a situation may effectively lead to the patient being injured by the medical instrument (for example to damage of healthy tissue of the anatomy of interest or to another part of the body of the patient by the medical instrument). Immediate measures can then be taken to avoid injuring the patient when such a situation is detected.

In particular embodiments, the tool guide of the medical robot comprises an actuator allowing the medical instrument to be released instantly. The actuator is commanded by the control unit of the medical robot. The control unit of the augmented-reality navigation system is configured to transmit to the control unit of the medical robot a command to instantly release the medical instrument when the risk-of-injury situation is detected.

In particular embodiments, the articulated arm has at least six degrees of freedom, so that several different candidate configurations of the articulated arm allow the surgical action to be performed with the medical instrument along the predetermined path. The control unit of the augmented-reality navigation system is configured to display, on the display device, in the form of augmented-reality content overlaid on the real images, said candidate configurations and to receive an indication relating to a selection, by the practitioner, of one particular configuration from among the various candidate configurations.

The various candidate configurations are overlaid on the real images and allow the practitioner to select one particular configuration such that the presence of the medical robot is of no (or little) hindrance during the surgical intervention.

In particular embodiments, when the medical instrument is inserted into the body of the patient along the predetermined path, the control unit of the augmented-reality navigation system is configured to display, on the display device, in the form of augmented-reality content overlaid on the real images, a part of the medical instrument which part is inserted into the body of the patient. To this end, the position of the medical instrument is, for example, detected by the control unit of the augmented-reality navigation system on the real images acquired by the camera using known algorithms of the "Computer Vision" type.

Using such arrangements, the practitioner is able to monitor continuously and in real time the insertion of the medical instrument into the anatomy of interest of the patient to the extent that the part of the medical instrument that is not visible to the naked eye is overlaid on the real images.

In particular embodiments, the control unit of the augmented-reality navigation system is configured to calculate and display on the display device, in the form of augmented-reality content overlaid on the real images, the distance between the medical instrument and a target point on the anatomy of interest and/or to detect an instant at which the medical instrument has reached said target point.

DESCRIPTION OF THE FIGURES

The invention will be better understood from reading the following description, given by way of nonlimiting example, and made with reference to FIGS. 1 to 10 which depict:

FIG. 1 a schematic depiction of one embodiment of an augmented-reality navigation system according to the invention, FIG. 2 a schematic depiction of a marker intended to be placed on the patient in proximity to the anatomy of interest, FIG. 3 a depiction of the movement followed by the marker during a period of recording in a plane XY of the coordinate system of the navigation system, FIG. 4 a continuous-line depiction of the movement followed by the marker along a main axis during a recording period, together with a broken-line depiction of a predictive model of the movement of the marker, FIG. 5 an illustration of the determination, during the recording period, of a first instant corresponding to an instant of acquisition of a pre-intervention medical image of the anatomy of interest of the patient, FIG. 6 an illustration of the determination of a second instant corresponding to a candidate instant for the insertion of a medical instrument, and of the comparison between the position of the marker at the first instant and the position of the marker at the second instant, FIG. 7 a schematic depiction of the generation of a three-dimensional anatomical model of the anatomy of interest from a pre-intervention medical image, FIG. 8 a schematic depiction of the real-time and continuous updating of the anatomical model according to the predictive model of the movement of the marker and according to a biomechanical model of anatomical structures of the human body, FIG. 9 an illustration of the collaboration between the augmented-reality navigation system according to the invention and a medical robot used to assist the practitioner in performing the surgical intervention, FIG. 10 a schematic depiction of the display, in the form of augmented-reality content, of several candidate configurations of the articulated arm of the medical robot that allow the surgical intervention to be performed.

In these figures, references that remain identical from one figure to another designate elements that are identical or analogous. For the sake of clarity, the elements depicted are not necessarily drawn to the same scale, unless mentioned otherwise.

DETAILED DESCRIPTION OF ONE EMBODIMENT OF THE INVENTION

Figure 1:
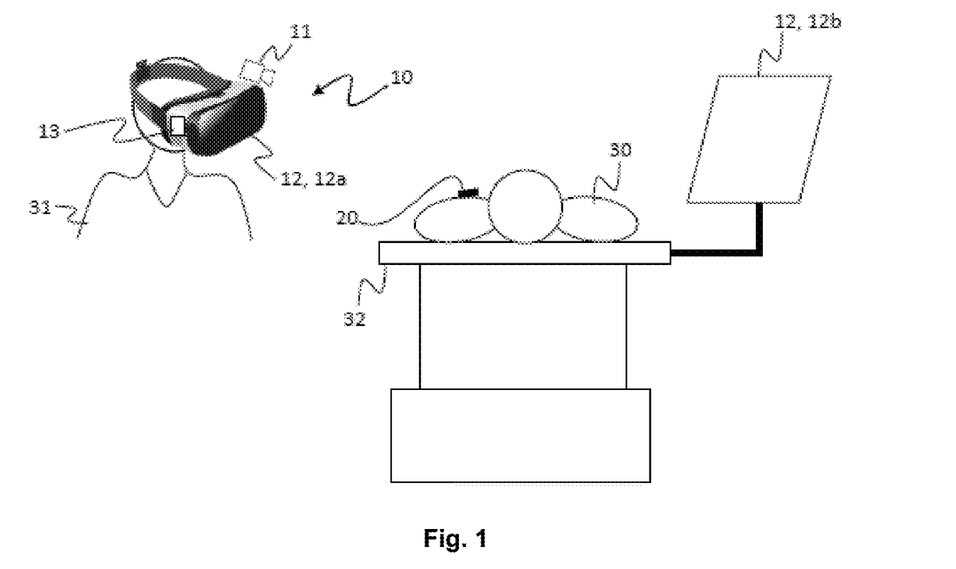

FIG. 1 schematically depicts one embodiment of an augmented-reality navigation system 10 for assisting a practitioner 31 in performing a surgical intervention on an anatomy of interest of a patient 30 resting on an intervention table 32.

The augmented-reality navigation system 10 comprises a camera 11 for acquiring real images. The camera 11 is intended to be worn by the practitioner on their head. In the example considered and illustrated in FIG. 1, the system 10 takes the form of an augmented-reality headset. The camera 11 is therefore integrated into the headset. Such arrangements allow the navigation system 10 to maintain a direct line of sight to the patient 30 for the camera 11. In particular, the practitioner 31 is unable to obstruct this direct line of sight (as they would be able to if the camera were mounted on a post in the room in which the intervention is being performed).

The augmented-reality navigation system 10 also comprises a display device 12 for displaying, in real time, the real images acquired by the camera 11, together with augmented-reality content overlaid on said real images. Advantageously, the display device 12 is also able to be worn by the practitioner on their head, directly in front of the eyes of the practitioner 31, as is the case in the example illustrated in FIG. 1 for which the display device is a display screen 12a integrated into the augmented-reality headset. Such arrangements allow the practitioner 31 to read information on the display device without having to avert their gaze from the patient 30. Alternatively or in addition, the display device 12 may also take the form of a display screen 12b, fixed for example to the intervention table 32, and visible by several individuals present in the room in which the intervention is being performed.

The augmented-reality navigation system 10 also comprises a control unit 13 connected to the camera 11 and to the display device 12. Conventionally, the control unit may be connected to the camera and to the display device 12 via wired communications means (notably when all of these elements are integrated into the augmented-reality headset worn by the practitioner) or via wireless communication means (for example when the display device 12b and/or the control unit 13 are sited at a distance).

The control unit 13 comprises one or more processors to run augmented-reality algorithms which operate on the "Computer Vision" principle to detect distinctive elements in the real universe and then superpose virtual content thereon. Alternatively or in addition, the control unit 13 comprises one or more programmable logic circuits (FPGAs, PLDs, etc.) and/or one or more specialist integrated circuits (ASICs) and/or a collection of discrete electronic components, etc., in order to run these algorithms. In other words, the control unit is configured by software and/or hardware means to run these augmented-reality algorithms.

The control unit 13 is notably configured to detect, on the real images, the position of a marker 20 placed on the patient 30 in proximity to the anatomy of interest.

The control unit 13 may also be configured to detect, on the real images, the position of a medical instrument manipulated by the practitioner, or held by a tool guide fixed to the end of an articulated arm of a medical robot used to assist the practitioner.

Figure 2:
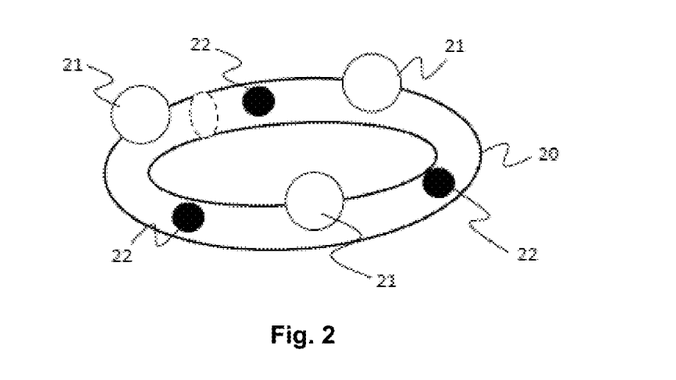

FIG. 2 schematically depicts such a marker 20 intended to be placed on the patient in proximity to the anatomy of interest. In the example considered and illustrated in FIG. 2, the marker 20 comprises three optical markers 21 of which the geometry and respective positions are known. Such arrangements make it possible to determine with precision the position of the marker 20 in a fixed frame of reference of the navigation system 10. This frame of reference is a three-dimensional coordinate system defined on the basis of a fixed object, such as, for example, the intervention table 32.

The marker 20 also comprises radiopaque markers 22 of which the geometry and respective positions are known, and which are visible in a pre-intervention medical image acquired by a medical imaging device (for example using computed tomography, magnetic resonance, ultrasound, tomography, position emission tomography, etc.). It is thus possible to determine with precision the position of a target anatomical zone of the anatomy of interest with respect to the position of the marker 20, and to plan the surgical intervention on the basis of the pre-intervention medical image. It is notably possible to define the position that a medical instrument is to adopt with respect to the position of the marker 20 in order to perform the surgical intervention.

The position of the anatomy of interest may, however, vary with respect to the position of the marker 20 as the result of the movements associated with the respiration of the patient, with internal deformations of the organ or with involuntary movements of the patient at the moment of the intervention. It is therefore appropriate to ensure that, when the surgical intervention is performed, the patient is in the same position or in the same phase of the respiratory cycle as they were at the moment at which the pre-intervention medical image was acquired.

To this end, the control unit 13 is configured to record the movement followed by the marker 20 during one or more respiratory cycles of the patient 30, to determine the position of the marker 20 at the instant at which the pre-intervention medical image is acquired (implicitly, this means that the control unit is configured firstly to determine the instant of acquisition of the pre-intervention medical image, and secondly to determine the position of the marker at said instant of acquisition), and to formulate a predictive model of the movement of the marker from the recorded movement. The predictive model of the movement of the marker then makes it possible to determine a second instant at which the medical instrument is to be inserted into the anatomy of interest of the patient. The second instant is determined in such a way that, at the second instant, the position of the marker 20 is substantially the same as the position of the marker 20 at the first instant. That makes it possible to ensure that, at the moment of insertion of the medical instrument (second instant), the patient is in the same position or in the same phase of the respiratory cycle as they were at the moment at which the pre-intervention medical image was acquired (first instant). The control unit 13 may be configured to compare the position of the marker at the first instant with the position of the marker at the second instant and to display a result of the comparison on the display device in the form of augmented-reality content overlaid on the real images.

Figure 3:
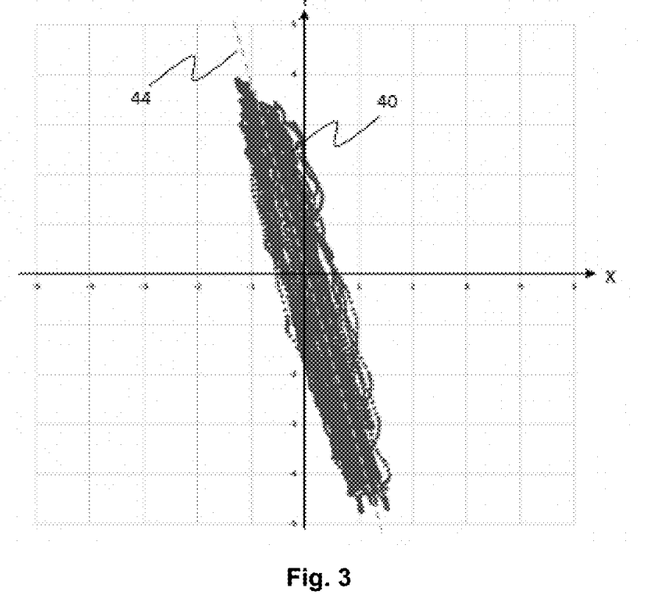

FIG. 3 depicts, by way of example, a recording of the movement 40 followed by the marker 20 during a recording period of predetermined duration corresponding to several respiratory cycles of the patient. Each point corresponds to a position adopted by the marker 20 over the course of time in a plane XY of the coordinate system of the navigation system 10. It may be noted, in this example, that the movement of the marker is mainly along the axis 44 plotted in dotted line in FIG. 3.

The movement 40 of the marker 20 is indicative of the movement of the rib cage of the patient as brought about by the respiration of the patient. For a better interpretation of the movement of the marker, and by analogy with the respiratory cycle of the patient, it is preferable to obtain a one-dimensional curve illustrating the oscillatory movement of the marker over the course of time. There are various methods that make it possible to obtain this one-dimensional curve. It might, for example, be conceivable to consider that the movement of the marker is predominantly vertical, and therefore to consider only the Y-axis. However, in such a case, some of the amplitude of the movement of the marker would be lost. In another example, it is conceivable to make an analysis of the positions of the marker in terms of their key components. The positions of the marker may notably be displayed according to a key component corresponding to the main axis 44 of the movement of the marker.

Figure 4:
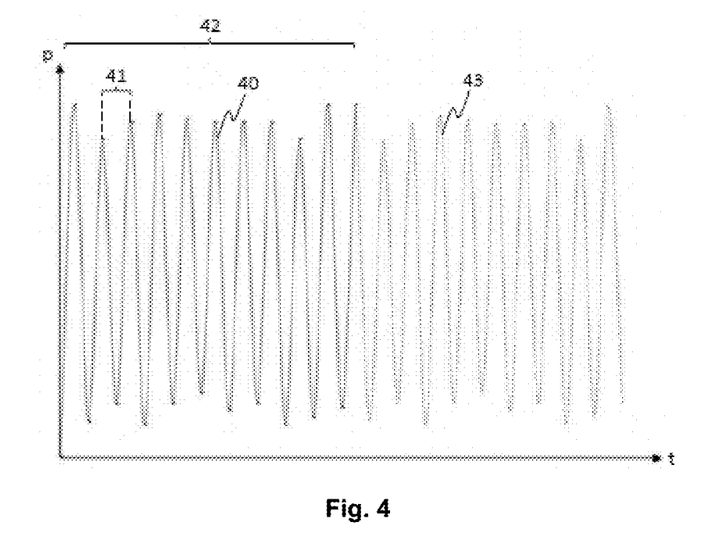

FIG. 4 depicts, in a continuous line, the movement 40 of the marker 20 during the recording period 42 along the main axis 44 over the course of time. The position p of the marker 20 along the main axis 44 is depicted along the ordinate axis; time is depicted on the abscissa axis. The recording period comprises several respiratory cycles 41 of the patient.

FIG. 4 also depicts, in a broken line, a predictive model 43 of the movement of the marker 20, which model is formulated from the movement 40 made by the marker 20 during the recording period 42. In the example considered and illustrated in FIG. 4, the predictive model 43 is a simple repeat of the movement 40 of the marker 20 recorded during the recording period 42. However, it should be noted that other methods may be envisioned for obtaining a predictive model of the movement of the marker. For example, it is conceivable to model a respiratory cycle corresponding to a mean of the respiratory cycles observed during the recording period. In variants, machine-learning algorithms may be used to formulate the predictive model of the movement of the marker from the movement of the marker as recorded during the recording period.

Figure 5:
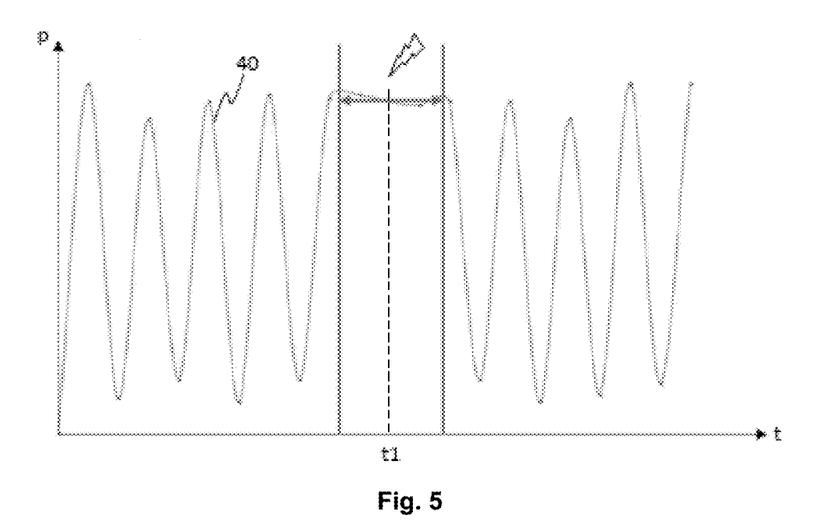

FIG. 5 illustrates the determination of a first instant t1 belonging to the recording period 42 and corresponding to the instant at which the pre-intervention medical image of the anatomy of interest of the patient is acquired. Remember that the pre-intervention medical image is acquired by a medical imaging device that does not form part of the navigation system according to the invention.

There are various methods that can conceivably be used so that the control unit 13 of the augmented-reality navigation system 10 is capable of determining the first instant t1. According to a first example, the medical imaging device may be connected to the control unit 13 of the navigation system 10, for example via wired communications means or wireless communications means. In that case, the medical imaging device may send an indication to the control unit 13 at the instant at which the pre-intervention medical image is acquired. According to a second example, the position of the marker 20 at the first instant t1 is automatically recorded by the control unit 13 when the patient enters a state of apnoea. In that case, the respiratory or the ventilation device is connected to the control unit 13 of the navigation system 10, for example via wired communications means or wireless communications means and sends the control unit 13 an indication as soon as the respiration of the patient is blocked or enters a state of apnoea. According to a third example, the position of the marker 20 at the first instant t1 is recorded manually by the operator when the patient is placed in a state of apnoea. According to a fourth example, the position of the marker 20 at the first instant t1 is recorded automatically by the control unit 13 as soon as the marker 20 has been substantially immobile for more than two seconds (a period corresponding for example to a plateau in the respiratory cycle at the end of inspiration or the end of expiration). According to a fifth example, an X-ray detector (for example a dosimeter or a scintillator) may be connected to the control unit 13 of the navigation system 10. In that case, the X-ray detector may send the control unit 13 an indication at the instant at which the pre-intervention medical image is acquired. For the second, third and fourth examples, the pre-intervention medical image is acquired at an instant at which the respiration of the patient is blocked. For the first and fifth examples, it is not essential for the pre-intervention medical image to be acquired at an instant at which the respiration of the patient is blocked.

In the example illustrated in FIG. 5, the first instant t1 corresponds to a median instant in the duration of acquisition of the medical image. It is therefore possible to determine the position adopted by the marker 20 at said instant t1. However, it should be noted that the first instant t1 could have a certain duration (the X-ray exposure time corresponding to the time taken to acquire the medical image, or even several consecutive medical images). In that case, the position adopted by the marker 20 at the first instant t1 may be determined from a mean of the positions adopted by the marker 20 during the X-ray exposure time. It is also conceivable for this mean to be weighted by the X-ray dose received in each position.

In the example illustrated in FIG. 5, the pre-intervention medical image is acquired at an instant at which the respiration of the patient is blocked. However, there is nothing to prevent the pre-intervention medical image from being, in another example, acquired to an instant at which the patient is breathing freely.

Figure 6:
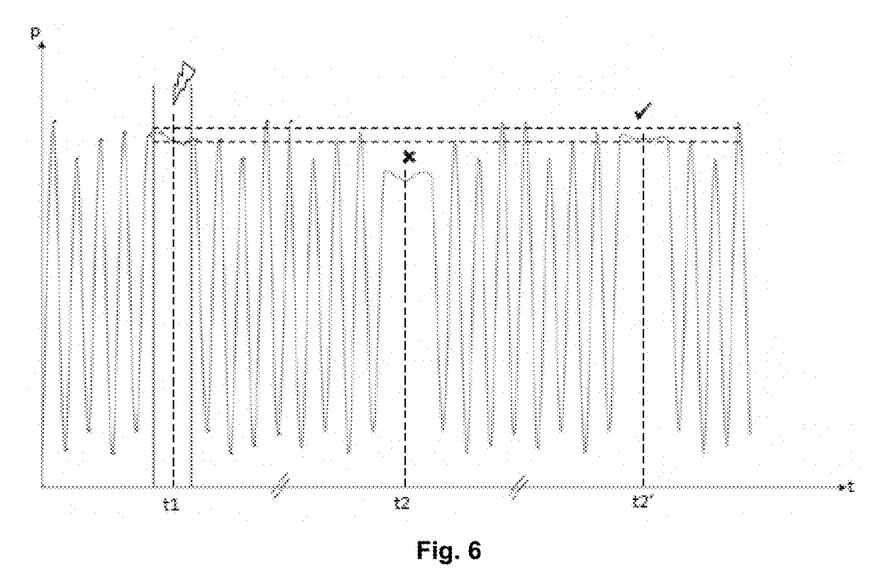

FIG. 6 illustrates the determination of a second instant t2 corresponding to a candidate instant for the insertion of a medical instrument, and the comparison between the position of the marker at the first instant t1 ("target" position) and the position of the marker at the second instant t2 ("candidate" position). The second instant t2 is determined from the predictive model so that the candidate position more or less corresponds to the target position. As illustrated in FIG. 6, the real movement of the marker 20 is monitored continuously. A comparison between the candidate position of the marker 20 at the instant t2 can therefore be made against the target position of the marker 20 at the instant t1. In the example illustrated in FIG. 6, it so happens that the candidate position is too far removed from the target position. A new second instant t2' is therefore determined from the predictive model. The position of the marker at the instant t2' is this time sufficiently close to the target position. That means that the surgical action (the insertion of the medical instrument) can take place at the instant t2' as planned on the pre-intervention medical image.

In order to make the comparison between a candidate position and the target position, a tolerance band is used. For example, it is considered that the candidate position is substantially identical to the target position if the candidate position is within ±10% of the target position. As a preference, a tolerance band of ±5% of the target position is used.

The result of the comparison is displayed on the display device 12 to indicate to the practitioner 31 whether or not it is a good time to proceed with inserting the instrument at the candidate instant considered.

In particular embodiments, the augmented-reality navigation system 10 is configured to collaborate with a medical robot used for assisting the practitioner in performing the surgical action, or to perform the surgical action directly, autonomously. The result of the comparison is then sent by the navigation system 10 to the medical robot in order, where appropriate, to activate the positioning of an articulated arm of the medical robot suitably for performing the surgical action.

Figure 7:
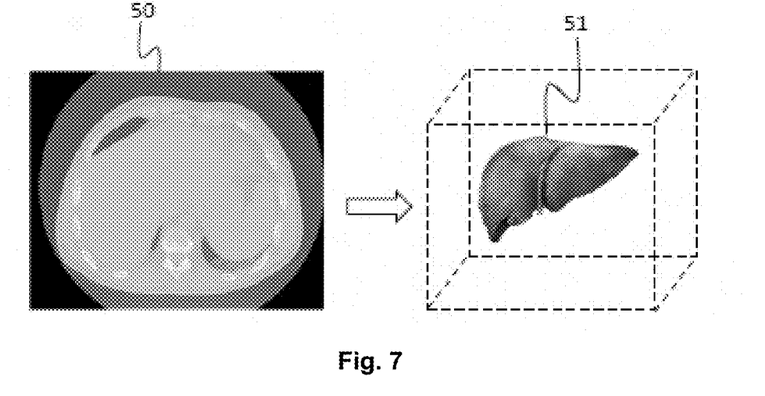
Figure 8:
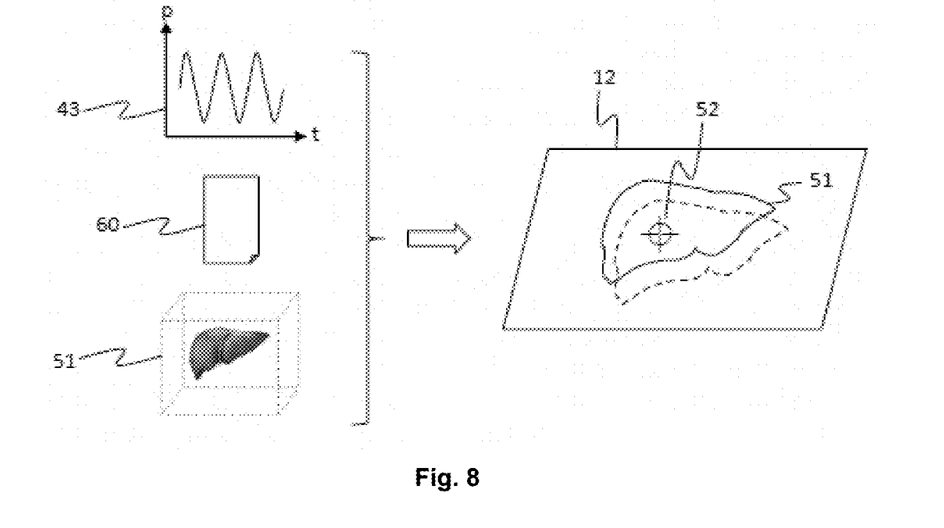

Independently of the determination of an opportune instant for performing the surgical action, and as illustrated in FIGS. 7 and 8, the predictive model 43 of the movement of the marker 20 may also be used to continuously and in real time update a three-dimensional anatomical model 51 of the anatomy of interest and which is generated by the control unit 13 from the pre-intervention medical image 50. This anatomical model can then be displayed on the display device 12 in the form of augmented-reality content overlaid on the real images.

To receive the pre-intervention medical image acquired by the medical imaging device, the control unit is connected to the imaging device via wired communication means or wireless communication means, for example. According to another example, the control unit may be connected to a peripheral memory device, for example a USB (acronym for "Universal Serial Bus") stick on which the pre-intervention medical image is stored.

In the example considered and illustrated in FIGS. 7 and 8, the anatomy of interest is the liver of the patient, and the surgical intervention seeks to ablate a tumour present in said anatomy of interest. The pre-intervention medical image 50 is acquired by performing a computed tomography (CT) scan. The instant at which the medical image is acquired, and the corresponding position of the marker 20 at this instant, are determined by the control unit 13 of the navigation system 10.

The control unit 13 is configured to display the anatomical model 51 on the display device 12 in the form of augmented-reality content overlaid on the real images. However, the movements brought about by the respiration of the patient cause the anatomy of interest to move. As illustrated in FIG. 8, the control unit is configured to allow the position of the anatomical model 51 to be updated continuously and in real time according to the predictive model 43 of the movement of the marker and according to a biomechanical model 60 of anatomical structures of the human body. Thus, the anatomical model 51 displayed on the display device 12 as an overlay on the real images moves in a manner synchronized to the respiration of the patient.

The position of the anatomical model 51 at the moment at which the pre-intervention medical image is acquired corresponds to a reference position of the anatomical model 51 with respect to a particular position of the marker 20. Thanks to the predictive model 43 of the movement of the marker 20 it is possible to anticipate the position that the marker 20 is going to adopt over the course of time. Thanks to the biomechanical model 60, it is possible to adjust the position of the anatomical model 51 according to the position adopted by the marker 20 over the course of time.

The biomechanical model 60 preferably includes the main anatomical structures of the thoracic-abdominal-pelvic region such as the thoracic and abdominal walls, the muscles, the tendons, the bones and joints, the organs, the vascular network, etc., and models of their deformations and mechanical interactions. The biomechanical model 60 also preferably takes account of the effects of gravity according to the position of the patient 30. Such biomechanical models are known from scientific literature, see, for example, the following publications:

"SOFA: A Multi-Model Framework for Interactive Physical Simulation", F. Faure et al., Soft Tissue Biomechanical Modeling for Computer Assisted Surgery—Studies in Mechanobiology, Tissue Engineering and Biomaterials, Volume 11, Springer, "A Personalized Biomechanical Model for Respiratory Motion Prediction", B. Fuerst et al., International Conference on Medical Image Computing and Computer Assisted Intervention, 2012, "Patient-Specific Biomechanical Model as Whole-Body CT Image Registration Tool", Mao Li et al., Medical Image Analysis, 2015, May, pages 22-34.

It should be noted that the biomechanical model of the human body is not necessarily specific to the patient concerned and may be a biomechanical model of a generic patient, for example of the same gender, size, body mass, etc. as the patient concerned and on which the surgical action is to be performed.

The control unit 13 integrates algorithms for harmonizing the biomechanical model 60 with the position of the marker 20 situated on the skin of the patient 30 in proximity to the anatomy of interest. For example, an algorithm makes it possible to propagate the movements of the skin surface to the internal volume and correctly calculate the position of the internal anatomical structures.

The control unit 13 may also be configured to display, on the anatomical model 51, in the form of augmented-reality content overlaid on the real images, an intended path to be followed by a medical instrument. The path is then updated in real time according to the position of the anatomical model. In the example illustrated in FIG. 8, the path comprises a target point 52 on the anatomy of interest. This target point 52 corresponds for example to the centre of the tumour to be treated. The path may also comprise a point of entry of the medical instrument at the surface of the anatomy of interest. The intended path to be followed by the medical instrument is generally defined on the basis of the pre-intervention medical image 50.

However, it is also conceivable for this path to be defined on a preoperative image, several days or even several months prior to the intervention. In that case, the control unit 13 is configured to realign the preoperative image with the pre-intervention image. To this end, the control unit may run conventional medical-image realignment and/or fusion algorithms.

The control unit receives the preoperative medical image via wired communication means or wireless communication means, for example. According to another example, the control unit may be connected to a peripheral memory device (for example a USB stick) on which the preoperative medical image is stored.

Certain elements may be segmented on the anatomical model 51, such as, for example, a region that is to be treated (the tumour that is to be ablated), an ablation region estimated on the basis of the treatment parameters, or ablation margins for the region that is to be treated (comparison between the region that is to be treated and the estimated ablation region). These elements may also be displayed in the form of augmented-reality content. Their positions are then updated in real time according to the position of the anatomical model.

In particular embodiments, the augmented-reality navigation system 10 comprises an interaction device allowing the practitioner 31 to interact with said system 10. The interaction device for example takes the form of a virtual-reality glove able to capture the exact position and pressure applied by the fingers and providing haptic feedback enabling the user to feel virtual objects. In another example, the interaction device may take the form of a stylus able to target a virtual object or a particular location on the anatomical model. The interaction device may notably enable the practitioner to define or modify the intended path to be followed by the medical instrument. The interaction device may also allow interaction with virtual objects such as setup menus, buttons, multiple-choice listings, etc., so as to define particular parameter values for the treatment to be performed (for example the type of treatment to be performed, the duration of the treatment, the power or the dose to be used for the treatment, etc.). Alternatively, the path that the medical instrument is to follow and/or the treatment parameters are determined automatically by machine-learning algorithms. The practitioner can then validate or modify the path and/or the treatment parameters proposed.

The position of certain augmented-reality content displayed on the display device 12 can be adapted according to the position of the head of the practitioner. For example, when the practitioner's head is bent to the left, certain virtual configuration objects displayed in augmented reality (notably virtual objects in the form of text) may be rotated counterclockwise so that these elements appear to the practitioner as if the head was not bent. The position of the head of the practitioner may notably be determined using a practitioner-head motion sensor or else directly from the position of the marker 20 on the real images.

Figure 9:
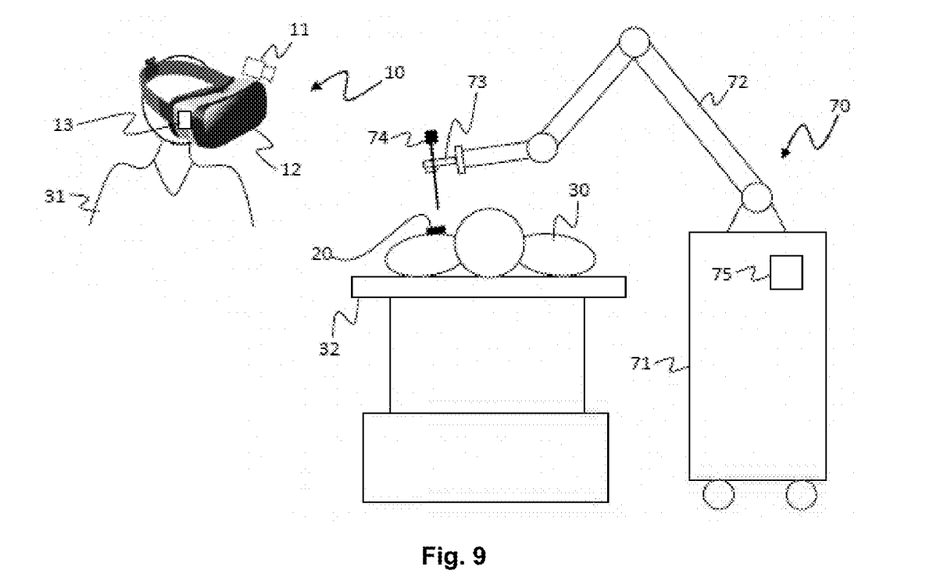

As illustrated in FIG. 9, the augmented-reality navigation system 10 may collaborate with a medical robot 70 used to assist the practitioner 31 during the surgical intervention. The medical robot comprises a mobile base 71, an articulated arm 72, and a control unit 75. One end of the articulated arm 72 is fixed to the mobile base 71 and the other end has a tool guide 73 intended to hold a medical instrument 74. The control unit 75 of the medical robot is configured to determine a configuration of the articulated arm that allows the medical instrument to perform a surgical action along a predetermined path. The configuration of the articulated arm is determined according to information relating to the position of the marker 20 which information is transmitted by the navigation system 10. The augmented-reality navigation system 10 and the medical robot 70 for example comprise communication means for exchanging messages. These communication means may be of the wired or wireless type.

The tool guide 73 consists for example of two grippers, driven by a linear actuator via two link rods so as to hold or release the medical instrument 74. The linear actuator may be reversible (the tool guide 73 may then be opened manually or automatically on command from the control unit 75) or irreversible (the tool guide 73 can be opened only automatically on command from the control unit 75). Advantageously, the tool guide 73 is able to guide medical instruments 74 of different diameters while maintaining the position of the guide axis of the medical instrument 74 and of releasing the medical instrument 74 laterally at any moment during the intervention. For example, such a tool guide 73 is able to guide instruments of which the outside diameter is between 11 and 21 gauge (G) (gauge is a unit of measurement commonly used to define the outside diameter of a medical instrument such as a needle, a probe or a catheter; 11 gauge corresponds to a diameter of 2.946 mm; 21 gauge corresponds to a diameter of 0.812 mm).

The medical action may be performed by the practitioner 31 (in which case the articulated arm 72 of the medical robot 70 is used chiefly to guide the medical instrument 74 to assist the practitioner in performing the medical action) or directly by the medical robot 70.

In the example considered, the information relating to the position of the marker corresponds to a predictive model indicative of the position of the anatomical model 51 during the course of the respiratory cycles of the patient. The control unit 75 of the medical robot 70 can therefore continuously and in real time adjust the configuration of the articulated arm 72 according to said predictive model indicative of the position of the anatomical model. Thus, the articulated arm 72 of the medical robot 70 remains constantly in a configuration that enables the planned surgical action to be performed.

Figure 10:
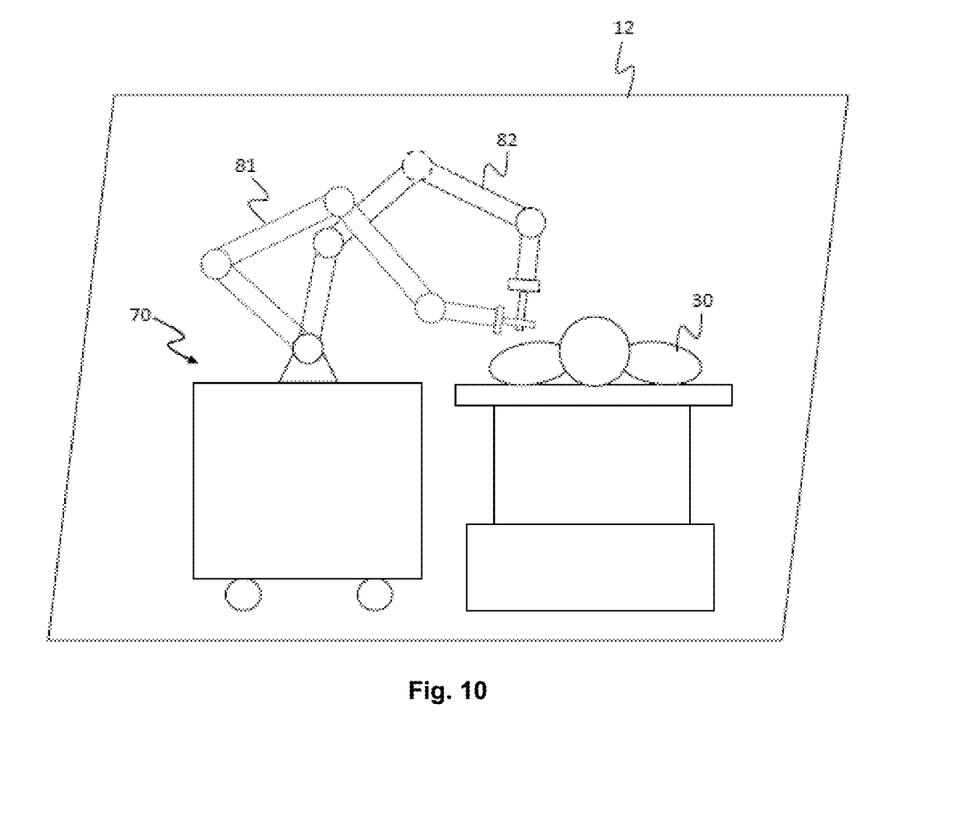

In particular embodiments, and as illustrated in FIG. 9, the articulated arm 72 has at least six degrees of freedom so that several different candidate configurations 81, 82 of the articulated arm allow the medical instrument 74 to perform the surgical action along the planned path. The control unit 13 of the augmented-reality navigation system is configured to display said candidate configurations 81, 82 on the display device 12 in the form of augmented-reality content overlaid on the real images. The practitioner can then select one of these candidate configurations using an interaction device (for example a virtual reality glove or stylus). The control unit 13 of the navigation system 10 can then communicate the selected configuration to the control unit 75 of the medical robot 70.

It may happen that the selected configuration for the articulated arm is not suitable because the body mass of the patient is too great. Also, during the course of the intervention, it is possible that the patient 30 might make an abrupt movement unexpectedly. In such instances, it is appropriate to ensure that the patient is not injured by undesired contact between the body envelope of the patient and the medical instrument or the articulated arm.

To this end, in particular embodiments, the control unit 13 of the augmented-reality navigation system 10 is configured to model an outer envelope of the body of the patient 30. The outer envelope of the body of the patient can be generated from the pre-intervention medical image 50 or from the anatomical model 51, possibly with the aid of data relating to the build of the patient. Alternatively or in addition, the outer envelope of the body of the patient may be determined on the real images acquired by the camera 11 of the navigation system 10 (via contour detection algorithms for example). The control unit 13 of the navigation system 10 is also configured to determine the position of the articulated arm 72 or of the tool guide 73 of the medical robot 70 and to detect a risk-of-collision situation when the distance between the articulated arm 72 or the tool guide 73 and the outer envelope of the body of the patient 30 is below a predetermined threshold. The control unit 75 may then be configured to interrupt the movement of the articulated arm 72 as soon as the distance between the articulated arm 72 or the tool guide 73 and the outer envelope of the patient is insufficient.

Alternatively or in addition, in particular embodiments, the control unit 13 of the augmented-reality navigation system 10 is configured to measure a deviation in the position of the marker 20 with respect to the predictive model 43 of the movement of the marker 20 (the deviation at a given instant corresponds for example to the distance between the real position of the marker at said instant and the position of the marker in the predictive model 43 for a corresponding instant in the respiratory cycle of the patient). The control unit 13 of the augmented-reality navigation system 10 is then configured to detect a situation in which there is a risk of injury from the medical instrument 74 when the deviation thus measured is above a predetermined threshold. Measures can then be taken to avoid injuring the patient when such a situation is detected. When the risk-of-injury situation is detected, the control unit 13 of the augmented-reality navigation system instantly transmits this information to the control unit 75 of the medical robot 70. The control unit 75 can then be configured to perform particular actions when the risk-of-injury situation is detected, such as for example commanding the actuator of the tool guide 73 to instantly release the medical instrument 74.

When the medical instrument 74 is inserted into the body of the patient 30 along the predetermined path, the control unit 13 of the augmented-reality navigation system can be configured to display, on the display device 12, in the form of augmented-reality content overlaid on the real images, a part of the medical instrument 74 that is inserted inside the body of the patient 30. It is also conceivable to calculate and to display the distance between the medical instrument 74 and a target point 52 on the anatomy of interest. It is also possible to detect an instant at which the medical instrument 74 reaches said target point 52 and to display an indication advising the practitioner of this.

The foregoing description clearly illustrates that, through its various features and the advantages thereof, the present invention achieves the set objectives namely of providing a solution for assisting a practitioner in a minimally-invasive surgical intervention while taking account in a reliable manner of the movements associated with the respiration of the patient or with involuntary movements of the patient during the course of the surgical intervention.

The invention claimed is:

1. An augmented-reality navigation system for assisting a practitioner when performing a surgical intervention on an anatomy of interest of a patient, said system comprising:
   a camera for acquiring real images, said camera being intended to be worn by the practitioner on their head,
   a display device for displaying, in real-time, the real images acquired by the camera together with augmented-reality content overlaid on said real images, and
   a control unit of the augmented reality navigation system connected to the camera and to the display device, wherein said control unit of the augmented reality navigation system is configured to:
   detect, on the real images, the position/orientation of a marker placed on the patient in the proximity of said anatomy of interest,
   record the movement followed by the marker during a recording period corresponding to one or more respiratory cycles of the patient,
   determine the position/orientation of the marker at a first instant (t1) belonging to said recording period and corresponding to an instant of acquisition of a pre-intervention medical image of the anatomy of interest of the patient by a medical imaging device,
   formulate a predictive model of the movement of the marker from the movement followed by the marker during the recording period;
   determine, from the predictive model, a second instant (t2) corresponding to a candidate instant of insertion of a medical instrument into the anatomy of interest of the patient,
   compare the position/orientation of the marker at the first instant (t1) with the position/orientation of the marker at the second instant (t2), and
   display a result of the comparison on the display device in the form of augmented-reality content overlaid on the real images.

2. The system according to claim 1, wherein the control unit of the augmented-reality navigation system is further configured to receive the pre-intervention medical image from the medical imaging device and to generate, from said pre-intervention medical image, a three-dimensional anatomical model of the anatomy of interest of the patient and to display said anatomical model on the display device in the form of augmented-reality content overlaid on the real images, the position/orientation of the anatomical model overlaid on the real images being updated continuously and in real time according to the predictive model of the movement of the marker and according to a biomechanical model of anatomical structures of the human body.

3. The system according to claim 2, wherein the control unit of the augmented-reality navigation system is further configured to display, on the anatomical model, in the form of augmented-reality content overlaid on the real images, an intended path to be followed by a medical instrument, said path being updated in real time according to the position/orientation of the anatomical model.

4. The system according to claim 3, wherein the intended path to be followed by the medical instrument is defined beforehand on a preoperative medical image, and the control unit of the augmented-reality navigation system is configured to receive said preoperative image and to realign the preoperative image to the pre-intervention medical image in order to display the path on the anatomical model.

5. The system according to claim 3, further comprising an interaction device allowing the practitioner to target a particular location on the anatomical model and wherein the intended path to be followed by the medical instrument is defined by the practitioner using the interaction device.

6. The system according to claim 2, wherein the control unit of the augmented-reality navigation system is configured to segment at least one element on the anatomical model from among the following elements:
different anatomical structures within the anatomy of interest,
a region to be treated within the anatomy of interest,
an ablation region estimated from parameters of the surgical intervention, and
ablation margins for a region to be treated within the anatomy of interest and determined by comparing the region to be treated and the estimated ablation region, and to display said segmented element on the anatomical model in the form of augmented-reality content overlaid on the real images, the segmented element being updated in real time according to the position/orientation of the anatomical model.

7. The system according to claim 1, wherein the control unit of the augmented-reality navigation system is configured to display, on the display device, in the form of augmented-reality content, at least one virtual configuration object regarding a surgical treatment parameter, and the system comprises an interaction device allowing the practitioner to interact with said virtual configuration object in order to select a particular value for said parameter.

8. The system according to claim 1, wherein the display device is a display screen integrated into an augmented-reality headset.

9. The system according to claim 1, wherein the control unit of the augmented-reality navigation system is configured to modify the position/orientation of augmented-reality content according to the position/orientation of the head of the practitioner.

10. The system according to claim 9, wherein the position/orientation of the head of the practitioner is determined using a practitioner-head motion sensor.

11. An assembly formed by an augmented-reality navigation system according to claim 1 and a medical robot for assisting a practitioner in a surgical intervention on an anatomy of interest of a patient, the medical robot comprising:
a mobile base,
an articulated arm of which one end is fixed to the mobile base and the other end has a tool guide intended to hold a medical instrument, and
a control unit configured to determine a configuration of the articulated arm that allows a surgical action to be performed with the medical instrument along a predetermined path, the configuration of the articulated arm being determined according to information relating to the position/orientation of the marker which information is transmitted by the navigation system.

12. The assembly according to claim 11, wherein the control unit is further configured to:
determine, from the predictive model, a second instant (t2) corresponding to a candidate instant of insertion of a medical instrument into the anatomy of interest of the patient,
compare the position/orientation of the marker at the first instant (t1) with the position/orientation of the marker at the second instant (t2), and
display a result of the comparison on the display device in the form of augmented-reality content overlaid on the real images, wherein the information relating to the position/orientation of the marker is an indication that the difference between the position/orientation of the marker at the first instant (t1) and the position/orientation of the marker at the second instant (t2) is below a predetermined threshold.

13. The assembly according to claim 11, wherein the control unit is further configured to receive the pre-intervention medical image from the medical imaging device and to generate, from said pre-intervention medical image, a three-dimensional anatomical model of the anatomy of interest of the patient and to display said anatomical model on the display device in the form of augmented-reality content overlaid on the real images, the position/orientation of the anatomical model overlaid on the real images being updated continuously and in real time according to the predictive model of the movement of the marker and according to a biomechanical model of anatomical structures of the human body, wherein the information relating to the position/orientation of the marker corresponds to a predictive model indicative of the position/orientation of the anatomical model during the respiratory cycles of the patient, and the control unit of the medical robot is configured to adjust, continuously and in real time, the configuration of the articulated arm according to said predictive model indicative of the position/orientation of the anatomical model.

14. The assembly according to claim 11, wherein the control unit of the augmented-reality navigation system is configured to:
model an outer envelope of the body of the patient,
determine the position/orientation of the articulated arm or of the tool guide of the medical robot, and
detect a situation in which there is a risk of collision when the distance between the articulated arm or the tool guide of the medical robot and the outer envelope of the patient is below a predetermined threshold.

15. The assembly according to claim 11, wherein the control unit of the augmented-reality navigation system is configured to detect a situation in which there is a risk of injury from the medical instrument when a deviation in the position/orientation of the marker with respect to the predictive model of the movement of the marker is above a predetermined threshold.

16. The assembly according to claim 15, wherein the tool guide of the medical robot comprises an actuator allowing the medical instrument to be released instantly, said actuator being commanded by the control unit of the medical robot, and the control unit of the augmented-reality navigation system is configured to transmit to the control unit of the medical robot a command to instantly release the medical instrument when the risk-of-injury situation is detected.

17. The assembly according to claim 11, wherein the articulated arm has at least six degrees of freedom, so that several different candidate configurations of the articulated arm allow the surgical action to be performed with the medical instrument along the predetermined path, and the control unit of the augmented-reality navigation system is configured to display, on the display device, in the form of augmented-reality content overlaid on the real images, said candidate configurations and to receive an indication relating to a selection, by the practitioner of one particular configuration from among the various candidate configurations.

18. The assembly according to claim 11, wherein, when the medical instrument is inserted into the body of the patient along the predetermined path, the control unit of the augmented-reality navigation system is configured to display, on the display device, in the form of augmented-reality content overlaid on the real images, a part of the medical instrument which part is inserted into the body of the patient.

19. The assembly according to claim 18, wherein the control unit of the augmented reality navigation system is configured to calculate and display on the display device, in the form of augmented-reality content overlaid on the real images, the distance between the medical instrument and a target point on the anatomy of interest and/or to detect an instant at which the medical instrument has reached said target point.

20. An augmented-reality navigation system for assisting a practitioner when performing a surgical intervention on an anatomy of interest of a patient, said system comprising:
- a camera for acquiring real images, said camera being intended to be worn by the practitioner on their head,
- a display device for displaying, in real-time, the real images acquired by the camera together with augmented-reality content overlaid on said real images, and
- a control unit of the augmented-reality navigation system connected to the camera and to the display device, wherein said control unit of the augmented-reality navigation system is configured to:
- detect, on the real images, the position/orientation of a marker placed on the patient in the proximity of said anatomy of interest,
- record the movement followed by the marker during a recording period corresponding to one or more respiratory cycles of the patient,
- determine the position/orientation of the marker at a first instant (t1) belonging to said recording period and corresponding to an instant of acquisition of a pre-intervention medical image of the anatomy of interest of the patient by a medical imaging device,
- formulate a predictive model of the movement of the marker from the movement followed by the marker during the recording period,
- determine, from the predictive model, a second instant (t2) corresponding to a candidate instant of insertion of a medical instrument into the anatomy of interest of the patient,
- compare the position/orientation of the marker at the first instant (t1) with the position/orientation of the marker at the second instant (t2), and
- display a result of the comparison on the display device in the form of augmented-reality content overlaid on the real images, wherein the information relating to the position/orientation of the marker is an indication that the difference between the position/orientation of the marker at the first instant (t1) and the position/orientation of the marker at the second instant (t2) is below a predetermined threshold.

* * * * *